(12) United States Patent
Gutierrez et al.

(10) Patent No.: US 7,186,756 B2
(45) Date of Patent: Mar. 6, 2007

(54) STEROID DERIVATIVES AND USE THEREOF AS MEDICAMENTS

(75) Inventors: Gilles Gutierrez, Lyons (FR); Mostafa Serrar, Villeurbanne (FR); Zohra Hadid, Venissieux (FR)

(73) Assignee: Inovat, Tunis (TN)

( * ) Notice: Subject to any disclaimer, the term of this patent is extended or adjusted under 35 U.S.C. 154(b) by 0 days.

(21) Appl. No.: 10/567,590

(22) PCT Filed: Jul. 23, 2004

(86) PCT No.: PCT/FR2004/001990

§ 371 (c)(1),
(2), (4) Date: Feb. 22, 2006

(87) PCT Pub. No.: WO2005/014614

PCT Pub. Date: Feb. 17, 2005

(65) Prior Publication Data

US 2006/0258753 A1  Nov. 16, 2006

(30) Foreign Application Priority Data

Jul. 25, 2003  (FR) .................................. 03 09099

(51) Int. Cl.
*A61K 31/12* (2006.01)
*C07C 49/00* (2006.01)

(52) U.S. Cl. ..................... 514/675; 560/258; 568/371

(58) Field of Classification Search ................. 514/675; 560/258; 568/371
See application file for complete search history.

(56) References Cited

U.S. PATENT DOCUMENTS 3,484,476 A * 12/1969 Fried et al. ................. 560/116

\* cited by examiner

*Primary Examiner*—Barbara P. Badio
(74) *Attorney, Agent, or Firm*—Charles A. Muserlian

(57) ABSTRACT

Steroids of the formula

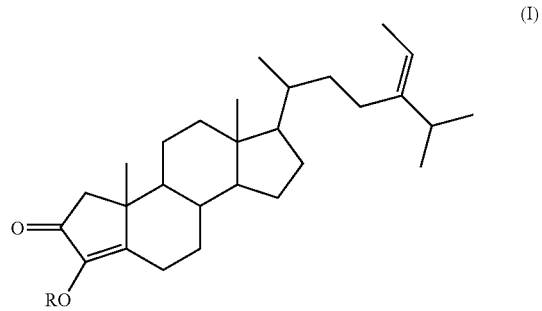

wherein R is defined as in the application capable of increasing the synthesis of collagen.

13 Claims, No Drawings

STEROID DERIVATIVES AND USE THEREOF AS MEDICAMENTS

SUMMARY

This application is a 371 of PCT FR 2004/001990 filed Jul. 23, 2004

This invention relates to the field of chemistry and more particularly to that of organic chemistry.

It has specifically as the subject matter novel A-nor steroids having the general formula I

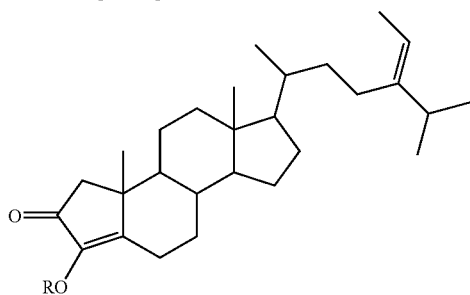

wherein R is hydrogen, a lower alkyl radical having from 1 to 7 atoms, a lower cycloalkyl radical having from 3 to 7 carbon atoms, an aryl radical having from 5 to 10 carbon atoms, an arylalkyl radical wherein the alkyl group has from 1 to 6 carbon atoms or an acyl moiety derived from an aliphatic carboxylic acid, a cycloalkyl carboxylic acid or an arylcarboxylic acid.

This invention has further as a subject the pharmaceutical compositions containing as the active ingredient, at least one compound of general formula I in admixture or mixed with a suitable excipient or vehicle.

The pharmaceutical compositions according to this invention may also contain another active ingredient having a similar or synergistic activity.

Use of the compounds of general formula I as drugs to promote the fixation of calcium by the osteoblasts.

Novel Steroidal Derivatives and Their Uses in Therapy

This invention relates to the field of chemistry and more particularly to that of organic chemistry.

More particularly it has as the subject matter novel steroids of semi-synthetic origin belonging to the family of A-nor steroids. Specifically it has as a subject novel steroids possessing the general formula I.

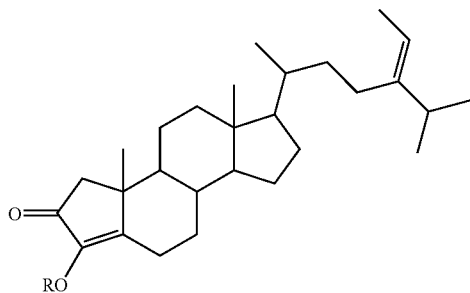

wherein R is a hydrogen, a lower alkyl radical having from 1 to 7 atoms, a lower cycloalkyl radical having from 3 to 7 carbon atoms, an aryl radical having from 5 to 10 carbon atoms, an arylalkyl radical wherein the alkyl group has from 1 to 6 carbon atoms or an acyl moiety derived from an aliphatic carboxylic acid, a cycloalkyl carboxylic acid or an arylcarboxylic acid.

Its chemical denomination is 2-oxo 3-OR A-nor 25-ethylidene cholest 3-ene.

Moreover the Keto-enol structure of this compound allows the formation of complexes such as for example the formation of a complex with iron, copper or zinc.

The compound of formula I for which R is a hydrogen, may exist in the form of one of the tautomeric forms of the keto-enol form depending on the medium and depending on the pH value. The ketonic form may enolize itself more or less fully to produce either a mixture ketone/enol either to a fully enolized compound enol+ketone.

An alkaline medium or the use of polar solvents are favourable factors for the enolization and the complete enolization of the molecule allows the production a 2-keto 3-enol compound pure and stable.

Among the compounds of general formula I it may be particularly cited:

2-oxo 3-hydroxy 25-ethylidene A-nor cholest-3-ene (R=H)
2-oxo 3-acetoxy 25-ethylidene A-nor cholest-3-ene (R=$CH_3CO$)
2-oxo 3 methoxy 25-ethylidene A-nor cholest-3-ene (R=$CH_3$)

which are the preferred compounds.

It is also possible to prepare a tetrahydropyranyl ether by reaction of dihydropyran in acidic medium, a benzylic ether by reaction of benzyl chloride or nitrobenzyl chloride in the presence of dimethyl formamide.

They may also be prepared various carboxylic esters such as a propionate, a valerate, a benzoate, a naphtoate, a terephtalate, a succinate, a malonate, a nicotinate, a glucuronate or a lactobionate.

The compounds of general formula I may be produced through hemi synthesis starting from fucosterol according to a process in which fucosterol is submitted to an oxidation into cholesten-5 3-one then oxidation by means of DDQ into cholest-5-en-2,3-dione and rearrangement in alkaline medium into 2-keto 3-hydroxy A-nor cholest-3-ene.

The formation of ethers starting from the 3-hydroxylated compound is performed using a diazoalkane in an inert solvent such as isopropyl ether or tetrahydrofuran or using an alkylating agent in basic medium.

The alkylating agent is preferably a halide a sulphate, or an alkyl tosylate, a cycloalkyl halide, an arylalkyl halide or an aryl halide.

The reaction is performed in the presence of pyridine, lutidine, collidine, dimethylformamide, dimethylacetamide, or even in the presence of 4-dimethylaminopyridine.

The esters of the compound of formula I may be prepared using the action of an acylating agent such as a functional derivative of an organic carboxylic acid, an acid halide, an acid anhydride or a mixed acid anhydride, in an aprotic polar solvent in the presence of a catalyst for acylation such as 4-dimethylaminopyridine or 4-hydroxybenzotriazole, on a 3-hydroxylated compound.

The structure of the compounds of formula I has been ascertained by determining the NMR spectrum and more particularly of the NMR spectrum using a high resolution apparatus (500 MHz) ([$^1$H]) proton NMR, [$^{13}$C] carbon NMR in HMBC, in NOE, in TOCSY and in NMR-LC.

An additional analysis using NMR of the [$^1$H] proton shows that the compound after having been kept in $CD_3OD$ at cold temperature, has not be decomposed.

The compound of formula I for which R is hydrogen may give rise to metallic complex with the metals of valency II, III or IV such as the complexes of iron, nickel, copper, zinc, manganese or chromium. These complexes may be used as a means for identifying, purifying or separating the compounds of formula I during physical analysis.

The compounds of formula I may also give rise to derivatives of the free ketonic function such as for example a ketal, a thioketal, a hemi-thioketal, an oxime, a o-carboxymethyl oxime, or an optically active or racemic dicarboxy alkylene ketal.

The compounds of general formula I present seven asymmetry centres and may therefore exist in different spatial structures. It may thus be possible that the function of B and C rings may present the natural configuration 9beta-8alpha or the antipodal configuration 9alpha-8beta depending on the synthesis conditions.

The configuration of the methyl compound 20 on the side chain is as a principle beta. The orientation may be inversed when desired.

The compounds of formula I may also be defined by the nature of the UV spectrum which shows a strong absorption at 220 and at 240 nm. Adding acid does not modify the UV absorption peaks. The alkaline products such as sodium carbonate, potash or lithium hydroxide cause a shift form 240 to 255 nm.

The compounds according to the invention may moreover be characterized using another analysis methods such as circular dichroism, infrared spectrum in dry state or dispersed in Nujol, thin layer chromatography or high performance liquid chromatography or rotatory power in ethanol.

As a commodity the compounds of formula I are called Maltadiolone and its esters. The basic molecule (R=H) is called Maltadiolone

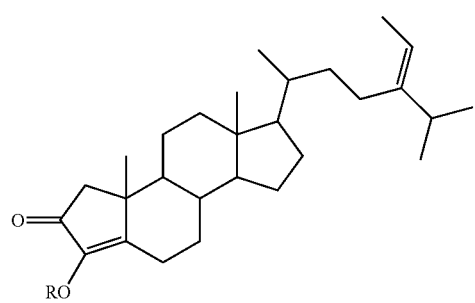
(I)

the maltane skeleton being defined as:

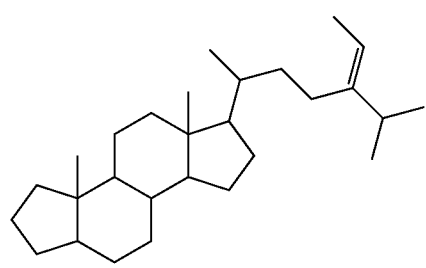
(II)

The compounds of general formula I show interesting biological properties which make them useful as active ingredients of drugs.

The substances according to the invention exert an influence of the synthesis of connective molecules such as the desmosomial proteins and the skin cytokeratins, even in the presence of corrosive agents such as sulphuric acid.

The compounds of general formula I distinguish themselves by noticeable properties on the repair of the extra cellular matrix. They increase the synthesis of collagen, they promote the synthesis of glysosaminoglycanes, even in the presence of deleterious substances such as the interleukins and namely interleukin IL-1.

As an example a culture of bone cells (line UMR 106 or G 292) treated with 10 ng of Maltadiolone show an increase in the fixed calcium, in comparison with the untreated control cells.

As an example a culture of bone cells (line URM 106 or G 292) will be treated with 5 µl of Interleukine-I (IL-1) i.e 1 ng per ml. The atomic spectrophotometry analysis of the bound calcium in the extra cellular matrix shows a level of 700 ng/ml in the control cells. This value is lowered to 25 ng/ml in the presence of IL-1.

In the same conditions the cells are treated with 10 □g Verapamil or any other inhibitor of the calcium such as Cinchonine or Diltiazem. It is stated that the amount of fixed calcium in the extra cellular matrix of the osteoblasts is equivalent to that of the cells treated with interleukin.

In the same conditions the cells treated with both 1 µg IL-1 and 10 µg Maltadiolone according to the invention, restore a fixative activity on the calcium, equivalent to that of cells untreated with a calcium inhibitor.

In the same conditions as previously, it has been determined that the activity of recovery of the fixation of calcium on the extra cellular matrix may be detected from 10 ng/ml.

This invention also relates to pharmaceutical compositions incorporating as the active ingredient at least one compound of general formula I in which R has the above given meanings in admixture or mixed with an excipient or a vehicle suitable for the administration per oral way, per parenteral way, by rectal way, by topic way, non toxic, pharmaceutically, acceptable.

For the digestive administration the compounds of general formula I, are offered in the form of uncoated or coated tablets, dragées, pills, aromatised or non-aromatised powders, soft gelatine capsules, or capsules.

For the parenteral administration, the compounds of general formula I are offered in the form of injectable solutions, injectable suspensions, injectable dispersions, in a water-in-oil emulsion or in a oil-in-water emulsion. A particularly suitable vehicle is an emulsion of medium chain fatty acids, marketed under the Trade Name of Intralipid.

The pharmaceutical compositions according to the invention may further contain another active ingredient having a calciotropic action, similar or synergistic, such as an estrogenic compound as for example estradiol, an ester of estradiol or an ether of estradiol such as Mestranol or quingestanol or a SERM.

The compounds of general formula I distinguish themselves with a high level of activity at low doses for a weak toxicity. The usual posology in compounds of general formula I ranges from 10 ng to 50 mcg/ml and preferably from 50 ng to 500 ng/ml. Phenomena of toxicity appear only at doses higher than 50 mcg/ml and indicate rather a overactivity of the products.

The following examples illustrate the invention without limiting it in any manner.

EXAMPLE I

Formulation of Tablets of 2-oxo 3-hydroxy 25-ethylidene A-nor cholest-3-ene

| | |
|---|---|
| Active ingredient | 100 □g |
| Lactose | 100 g |
| Microcristalline Cellulose | 25 g |
| Polyvinyl pyrolidone K | 30 g |
| Sorbitol | 10 g |
| Calcium sulphate | 25 g |

For 1000 Tablets

EXAMPLE II

Formulation of Tablets of 2-oxo 3-hydroxy 25-ethylidene A-nor choles 3-ene

| | |
|---|---|
| Active ingredient | 2.25 mg |
| Mannitol | 5 mg |
| Sugar syrup | 10 mg |
| Magnesium Carbonate | 500 g |
| Talc | 15 g |

The powders are compressed on STOKES rotating machines to produce 70 mg tablets.

EXAMPLE III

Formulation of Tablets of 2-oxo 3-methoxy 25-ethylidene A-nor cholest 3-ene

| | |
|---|---|
| Active ingredient | 250 □g |
| Calcium carbonate | 300 g |
| Microcristalline cellulose | 20 g |
| Poly (ethylene oxide) sold under the brand name Pluronic F88 | 20 g |
| Colloidal silica | 15 g |

*for 1000 tablets

EXAMPLE IV

Injectable Solution of 2-oxo-3-acetoxy-25-ethylidene A-nor cholest 3-ene

| | |
|---|---|
| 2-oxo 3-methoxy 25-ethylidene A-nor cholest 3-ene | 5 mg |
| Intralipid | 250 ml |
| Distillated water | 500 ml |

This solution is filled in 2 ml ampoules. It is filtered on membranes and it is sterilized for ten minutes at 120° C.

This ampoules are distributed in rigid cases, tips downwards. Applying the vacuum the ampoules are filled, they are wiped, dried and the tips are soldered in sterile atmosphere.

EXAMPLE V

Tablets of Ferrous Complex of 2-oxo 3-hydroxy 25-ethylidene A-nor cholest-3-ene 0.82 g of 2-oxo 3-hydroxy 25-ethylidene A-nor cholest-3-ene are solubilized in 25 ml dimethylformamide. This solution is diluted with an equal volume of water then without delay 10 ml of a 5% solution of ferrous sulphate in dilute sulphuric acid are added. The whole mixture is strongly mixed, then kept aside for a night.

The formed precipitate is separated on a crucible of fritted glass. It is rinsed several times with water then twice consecutively with acetone —1.02 g of ferrous complex is thus collected which is dried in ventilated oven at 80° C.

After a night of stay, the complex witch occurs in the form of dark-brown cristals is collected.

0.100 g of ferrous complex is weighed together with 500 g lactose. It is carefully homogenized then 40 g microcrystalline cellulose and 25 g colloidal silica (Aerosil 200) and finally 4 g magnesium stearate are added. The powder after homogenization is sieved on a 200-mesh sieve. With this powder are produced soft gelatine capsules containing 4 mcg of active ingredient per unit dosage.

What is claimed is:

1. A steroid of the formula

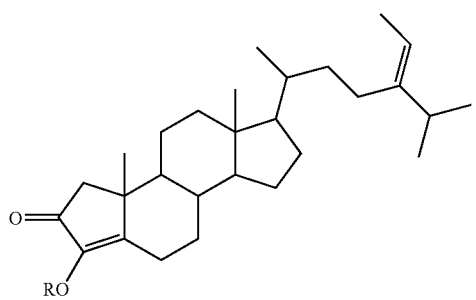

(I)

wherein R is selected from the group consisting of hydrogen, lower alkyl of 1 to 7 carbon atoms, lower cycloalkyl of 3 to 7 carbon atoms, aryl of 5 to 10 carbon atoms, aryl alkyl wherein the alkyl has 1 to 6 carbon atoms, acyl of an aliphatic carboxylic acid.

2. The tautomeric forms of a steroid of claim 1.

3. A metallic complex of the compound of claim 1 wherein R is hydrogen.

4. A steroid of claim 1, wherein the ketonic function is blocked in the form of a member selected from the group consisting of ketal, thioketal, hemithioketal, oxime or optically-active or racemic (dicarboxyalkylene)ketal.

5. A compound of claim 1, that is 2-oxo 3-hydroxy 25-ethylidene-A-nor-cholest-3-ene.

6. A compound of claim 1, which is 2-oxo 3-acetoxy 25-ethylidene-A-nor-cholest-3-ene.

7. A compound of claim 1, which is 2-oxo 3-methoxy 25-ethylidene-A-nor-cholest-3-ene.

8. A process for the preparation of a compound of claim 1 wherein R is other than hydrogen or acyl comprising reacting a compound of formula I wherein R is hydrogen in an inert solvent with a diazoalkane selected from the group consisting of halide, sulfate and a tosylate of alky, cycloalkyl, aryl or aralkyl.

9. A process for the preparation of a compound of formula I of claim 1 wherein R is acyl of an aliphatic carboxylic acid comprising reacting a compound of claim 1 wherein R is hydrogen with an acylating agent of an aliphatic carboxylic acid in a polar aprotic solvent in the presence of an acylating catalyst.

10. A method of increasing the synthesis of collagen in warm-blooded animals comprising administering to a warm-blooded animal in need thereof a composition containing an effective amount of a compound of claim 1.

11. The method of claim 10 wherein the composition is applied to the skin of the warm-blooded animal.

12. The method of claim 10 wherein the composition also contains an estrogenic compound.

13. The method of claim 12 wherein the estrogenic compound is selected from the group consisting of estradiol and an ether of estradiol.

* * * * *